US00PP11415P

United States Patent [19]

Trees

[11] Patent Number: Plant 11,415

[45] Date of Patent: Jun. 13, 2000

[54] NEW GUINEA IMPATIENS PLANT NAMED 'BFP-844'

[75] Inventor: Scott C. Trees, Nipomo, Calif.

[73] Assignee: Ball Floraplant, A division of Ball Horticultural Co., West Chicago, Ill.

[21] Appl. No.: 09/113,138

[22] Filed: Jul. 9, 1998

[51] Int. Cl.[7] ..... A01H 5/00

[52] U.S. Cl. ..... Plt./318

[58] Field of Search ..... Plt./318

[56] References Cited

U.S. PATENT DOCUMENTS

P.P. 4,261 6/1978 Ryan ..... Plt./318
P.P. 9,137 5/1995 Kientzler ..... Plt./318

*Primary Examiner*—Howard J. Locker
*Assistant Examiner*—Wendy A Baker
*Attorney, Agent, or Firm*—C. A. Whealy

[57] ABSTRACT

A new and distinct cultivar of New Guinea Impatiens plant named 'BFP-844', characterized by its pink-colored flowers; compact, upright and mounded plant habit; good basal branching; and shiny dark green leaves.

1 Drawing Sheet

BACKGROUND OF THE INVENTION

The present invention relates to a new and distinct cultivar of New Guinea Impatiens plant, botanically known as *Impatiens hawkeri,* and hereinafter referred to by the cultivar name BFP-844.

The new New Guinea Impatiens is a product of a planned breeding program conducted by the Inventor in Arroyo Grande, Calif. The objective of the breeding program was to develop new cultivars with excellent basal branching, upright and medium growth habit, numerous large flowers, and interesting flower and foliage colors.

The new cultivar originated from a cross made by the Inventor of two unidentified proprietary *Impatiens hawkeri* selections. The cultivar BFP-844 was discovered and selected by the Inventor as a flowering plant within the progeny of the stated cross in a controlled environment in Arroyo Grande, Calif., on Sep. 15, 1996.

Asexual reproduction of the new cultivar by terminal cuttings taken at Arroyo Grande, Calif., has shown that the unique features of this new Impatiens are stable and reproduced true to type in successive generations of asexual reproduction.

SUMMARY OF THE INVENTION

The following traits have been repeatedly observed and are determined to be the unique characteristics of 'BFP-844'. These characteristics in combination distinguish 'BFP-844' as a new and distinct cultivar:

1. Pink-colored flowers.
2. Compact, upright and mounded plant habit.
3. Good basal branching.
4. Shiny dark green leaves.

The new New Guinea Impatiens can be compared to the commercial cultivar, BSR-152 Dark Pink (disclosed in U.S. Plant Pat. No. 8,409). However, in side-by-side comparisons conducted by the Inventor in Arroyo Grande, Calif., plants of the new New Guinea Impatiens differ from plants of the cultivar BSR-152 Dark Pink in the following characteristics:

1. Leaves of plants of the new New Guinea Impatiens are broader and lower leaf surfaces are darker red in color than leaves of plants of the cultivar BSR-152 Dark Pink.

2. Flowers of plants of the new New Guinea Impatiens are more flat and lighter pink in color than flowers of plants of the cultivar BSR-152 Dark Pink.

3. Plants of the new New Guinea Impatiens have fewer flowers per plant than plants of the cultivar BSR-152 Dark Pink.

4. Plants of the new New Guinea Impatiens have longer peduncles than plants of the cultivar BSR-152 Dark Pink. Moreover, peduncles of plants of the new New Guinea Impatiens are reddish whereas peduncles of plants of the cultivar BSR-152 Dark Pink are light green in color.

A detailed comparison of plants of the cultivar BFP-844 and the cultivar BSR-152 Dark Pink appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical plant of 'BFP-844'. Flower and foliage colors in the photograph may appear different from the actual colors due to light reflectance.

DETAILED BOTANICAL DESCRIPTION

The cultivar BFP-844 has not been observed under all possible environmental conditions. The phenotype may vary somewhat with variations in environment such as temperature and light intensity, without, however, any variance in genotype. The following observations, measurements and comparisons describe plants grown 10-cm pots in Arroyo Grande, Calif., under commercial practice in a glass-covered greenhouse with day temperatures about 22° C. and night temperatures about 18° C.

In the following description, color references are made to The Royal Horticultural Society Colour Chart except where general terms of ordinary dictionary significance are used.

Botanical classification: *Impatiens hawkeri* cultivar BFP-844.

Parentage:

*Male parent.*—Unidentified proprietary *Impatiens hawkeri* selection.

*Female parent*.—Unidentified proprietary *Impatiens hawkeri* selection.

Propagation:

*Type cutting*.—Terminal cuttings.

*Time to initiate roots*.—About 7 days at temperatures about 18° C.

*Time to develop roots*.—About 21 days at temperatures about 18° C.

*Rooting habit*.—Fibrous, fine, freely branching.

Plant description:

*Plant form*.—Compact, upright and mounded.

*Growth and branching habit*.—Moderately vigorous. Good basal branching with about five lateral branches at the base, dense and bushy growth. Appropriate for 10 and 12.5-cm. containers.

*Crop time*.—About ten weeks are required to produce a finished flowering plant in a 10cm. container from a rooted cutting.

*Plant height*.—About 10.6 cm.

*Lateral branches*.—Length: About 4.9 cm. Diameter: About 4.5 mm. Internode length: About 3 cm. Color: 183C with small green, 144C, areas.

*Foliage description*.—Leaves simple, generally symmetrical, abundant, in whorls or opposite. Quantity of leaves per lateral branch: About 11. Length: About 9.9 cm. Width: About 4.2 cm. Shape: Broadly elliptic with acuminate apex, acute base and serrate margin. Texture: Shiny, smooth, glabrous. Color: Fully expanded foliage, upper surface: 137A/137B. Fully expanded foliage, lower surface: 183B. Midvein, upper surface: Towards base, 51C, becoming light green, 154D, towards apex. Midvein, lower surface: 182C. Petiole: Length: About 1.5 cm. Diameter: About 2.5 mm. Color: Upper surface, 145C, lower surface, 51C.

Flower description:

*Flower type and habit*.—Pink-colored flowers. Freely and continuously flowering. Flowers arise from leaf axils. Usually about nine flowers and flower buds per lateral branch. Flowers positioned mostly above the foliage and typically face upright. Flowers generally flat and rounded. Flowers persistent.

*Flowering season*.—Year-round under greenhouse conditions. In the garden, flowering is continuous from spring until fall.

*Flower longevity*.—About one week.

*Flower size*.—Diameter: About 6 cm. Depth: About 1 cm.

*Flower buds*.—Length: About 1.9 cm. Diameter: About 1.1 cm. Shape: Ovoid, pointed. Color: 53A.

*Petals*.—Quantity: Five, overlapping. Length: About 3 cm. Width: About 3 cm. Shape: Obcordate with emarginate apex, attenuate base and entire margin. Texture: Smooth, very iridescent. Color: Upper petals, upper surface: Between 51B and 52B towards margin; 51A towards center; eye zone, between 63A and 64B. Lower petals, upper surface: Between 51B and 52B; eye zone, between 63A and 64B. Fully opened, lower surface: Between 52C and 55B; 52B towards center; midvein, 63A. Upper surface fading to: 58C.

*Spur*.—Length: About 6 cm. Shape: Narrow and curved. Color: 53A.

*Peduncles*.—Length: About 4.5 cm. Angle: About 30° to the lateral branch. Strength: Moderately strong. Color: 180A.

*Reproductive organs*.—Androecium: Stamen number: Five, anthers fused, filaments free. Anther shape: Obovate. Anther color: Lighter than 62D, translucent. Amount of pollen: Moderate. Pollen color: 10D. Gynoecium: Five-loculate fused. Stigma color: 61C. Ovary color: 144B.

Disease resistance: Under commercial conditions, resistance to pathogens has not been observed.

Seed development: Seed production has not been observed.

CHART A

| CHARACTERISTIC | 'BFP-844' | 'BSR-152 DARK PINK' |
|---|---|---|
| PLANT HEIGHT | About 10.6 cm | About 11 cm |
| LATERAL BRANCH DIAMETER | About 4.5 mm | About 3.5 m |
| STEM COLOR | 183C, with small green, 144C, areas | 183B |
| LEAF SHAPE | Broadly elliptic | Elliptic |
| LEAF LENGTH | About 9.9 cm | About 10 cm |
| LEAF WIDTH | About 4.2 cm | About 3.5 cm |
| LEAF COLOR, UPPER SURFACE | 137A/137B | 139A/135A |
| LEAF COLOR, LOWER SURFACE | 183B | 185A |
| LEAF VEIN COLOR, UPPER SURFACE | 51C | 51C |
| LEAF VEIN COLOR, LOWER SURFACE | 182C | 185A |
| PETIOLE DIAMETER | About 2.5 mm | About 3 mm |
| PETIOLE COLOR | Upper surface: 145C<br>Lower surface: 51C | Upper surface: 51C<br>Lower surface: 183C |
| QUANTITY OF FLOWERS AND FLOWER BUDS PER LATERAL BRANCH | About 9 | About 14 |
| FLOWER ASPECT | Flat | Slightly cupped |
| PETAL LENGTH | About 3 cm | About 2.5 cm |
| PETAL WIDTH | About 3 cm | Abour 2.1 cm |
| PETAL COLOR, OPENED, UPPER SURFACE | 52A/52B | 66C |
| PETAL COLOR, OPENED, LOWER SURFACE | 52B/52C; midvein, 53A | 58C |
| PETAL COLOR, FADING TO | 58C | 62A |
| PEDUNCLE LENGTH | About 4.5 cm | About 3.9 cm |
| PEDUNCLE COLOR | 180A | 145C |
| FLOWER BUD COLOR | 53A | 61D |

It is claimed:

1. A new and distinct cultivar of New Guinea Impatiens plant named 'BFP-844', as illustrated and described.

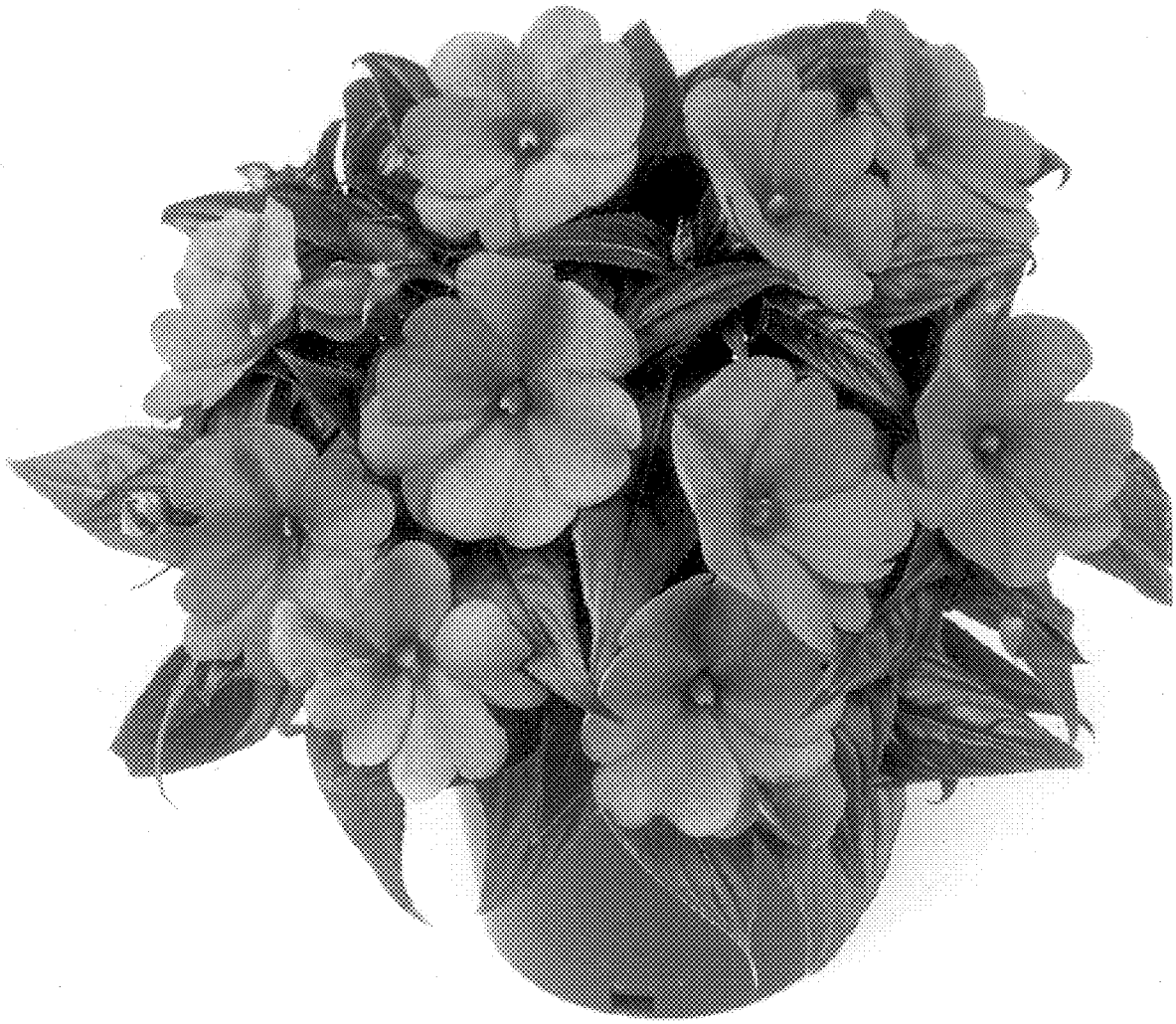

* * * * *